United States Patent [19]
Uchida et al.

[11] Patent Number: 5,516,675
[45] Date of Patent: May 14, 1996

[54] SEPARATION OF LACTOPEROXIDASE, SECRETORY COMPONENT AND LACTOFERRIN FROM MILK OR WHEY WITH A CATION EXCHANGE RESIN

[75] Inventors: Toshiaki Uchida, Kawagoeshi; Kaoru Sato, Kamifukuoka; Yoshihiro Kawasaki, Kawagoe; Shun'ichi Dosako, Urawa, all of Japan

[73] Assignee: Snow Brand Milk Products, Co., Ltd., Sapporo, Japan

[21] Appl. No.: 214,012

[22] Filed: Mar. 15, 1994

Related U.S. Application Data

[63] Continuation of Ser. No. 9,300, Jan. 26, 1993, abandoned.

[30] Foreign Application Priority Data

Jan. 29, 1992 [JP] Japan ................. 4-036915

[51] Int. Cl.$^6$ ............... C12N 9/08; C07K 3/00; A23J 1/00; A23C 23/00
[52] U.S. Cl. ............ 435/192; 426/580; 435/815; 530/395; 530/415; 530/417
[58] Field of Search ............. 435/240.27, 192, 435/183, 815; 426/580; 530/395, 415, 417

[56] References Cited

U.S. PATENT DOCUMENTS

| | | | |
|---|---|---|---|
| 4,668,771 | 5/1987 | Kawakami et al. | 530/366 |
| 4,791,193 | 12/1988 | Okonogi et al. | 530/416 |
| 5,149,649 | 9/1992 | Burling | 435/192 |

FOREIGN PATENT DOCUMENTS

| | | | |
|---|---|---|---|
| 0284525 | 9/1988 | European Pat. Off. | A23J 1/20 |
| 0418704A1 | 3/1991 | European Pat. Off. | A23J 1/20 |
| 0446876A2 | 9/1991 | European Pat. Off. | C07K 3/02 |
| WO89/04608 | 6/1989 | WIPO | A23J 1/20 |
| WO92/16625 | 10/1992 | WIPO | C12N 15/15 |

OTHER PUBLICATIONS

Buzila et al Revue Roumaine de Biochimie 1984 21(2) pp. 81–91 Abstract.

Li–Chan, et al., "Isolation of Immunoglobulins by Competitive Displacement of Cheese Whey Proteins During Metal Chelate Interaction Chromatography", J. Dairy Sci. 73: 2075–2086 (1990).

Al–Mashikhi, et al., "Isolation of Bovine Immunoglobulins and Lactoferrin from Whey Proteins by Gel Filtration Techniques", J. Dairy Sci., 70: 2486–2492 (1987).

Hirai et al., "Concentrations of Lactoferrin and Iron in Human Milk at Different Stages of Lactation", J. Nutr. Sci. Vitaminol, 36: 531–544 (1990).

Hutchens et al., "Rapid purification of porcine colostral whey lactoferrin by affinity chromatography on single–stranded DNA–agarose*. Characterization, amino acid composition and N–terminal amino acid sequence", Biochimica et Biophysica Acta, 999: 323–329 (1989).

Hutchens et al., "Interaction of Human Lactoferrin with DNA: One–Step Purification by Affinity Chromatography on Single–Stranded DNA–Agarose" Pediatric Research, 26(6): 618–622 (1989).

Kobayashi et al., "Esterase Activity Associated with Secretory IgA and Free Secretory Component Preparations From Human Milk", Biochimica et Biophysica Acta, 317: 517–523 (1973).

Rejman et al., "Purification and Characterization of Bovine Lactoferrin From Secretions of the Involuting Mammary Gland: Identification of Multiple Molecular Weight Forms", Comp. Biochem. Physiol., 93B, No. 4: 929–934 (1989).

Swan et al., "Separation of Proteins in Human Milk", Journal of Liquid Chromatography, 11(16): 3385–3392 (1988).

Woodhouse et al., "Quantitation of the Major Whey Proteins in Human Milk, and Development of a Technique to Isolate Minor Whey Proteins", Nutrition Research, 8: 853–864 (1988).

Woodhouse et al., "Quantitation of the Major Whey Proteins and Isolation of the Remaining Whey Protein Fraction by Immunoaffinity Chromatography", Federation Proceedings, 44(4), Mar. 5, 1985.

Yoshida, et al., "Isolation of Lactoperoxidase and Lactoferrins from Bovine Milk Acid Whey by Carboxymethyl Cation Exchange Chromatography", J. Diary Sci., 74: 1439–1444 (1991).

Primary Examiner—David M. Naff
Attorney, Agent, or Firm—Testa, Hurwitz & Thibeault

[57] ABSTRACT

Lactoperoxidase, secretory component and lactoferrin are separated in high purity from milk and related materials such as whey with a single cation exchange resin. After adsorption on the cation exchange resin, elution is carried out with an aqueous solution having an ionic strength and pH selected to elute each separately. Lactoperoxidase is eluted first, secretory component second and lactoferrin last. Each is obtained in a purity of about 80% or greater. The cation exchange resin can be a cross-linked polysaccharide, cellulose or an acrylamide resin having carboxyl, sulfonic acid or phosphoric acid functional groups which may be attached with a spacer. The separated lactoperoxidase, secretory component and lactoferrin are biologically active and can be used in pharmaceuticals, cosmetics, foods, drinks and feeds.

12 Claims, No Drawings

SEPARATION OF LACTOPEROXIDASE, SECRETORY COMPONENT AND LACTOFERRIN FROM MILK OR WHEY WITH A CATION EXCHANGE RESIN

This is a continuation application Ser. No. 08/099,300 filed on Jan. 26, 1993 now abandoned.

BACKGROUND OF THE INVENTION

This invention relates to the isolation and purification of biologically active substances from milk and related raw materials. More Particularly, this invention relates to treatments of the milk and related raw materials containing at least one of lactoperoxidase (LPO), secretory component (SC) and lactoferrin (LF) with an ion exchange chromatography to separate and produce them, respectively.

The lactoperoxidase, secretory component and lactoferrin obtained by the present invention have various physiological activities and may be used for pharmaceuticals, cosmetics, foods and drinks, and feeds.

DESCRIPTION OF THE PRIOR ART

Lactoperoxidase, secretory component and lactoferrin are glycoproteins existing in external secretions such as milk. Lactoperoxidase plays an important role for the removal of peroxides as well as a bactericidal activity. Secretory component associates with immunoglobulin A (IgA) and forms secretory immunoglobulin A (SIgA). The secretory immunoglobulin A is the most important factor that prevents from infectious diseases for infants, because it becomes resistant to proteolytic degradation in their digestive tracts. The secretory immunoglobulin A is, therefore, responsible for the coagulation action against exogenous antigens and prevention of local infection. The protease resistance of secretory immunoglobulin A is provided by secretory component. Lactoferrin has various physiological functions such as bacteriostatic activity, proliferation of lymphocytes, promotion of iron absorption, modulation of leukocyte differentiation, inhibition of lipid peroxidation, and antiviral activity. Thus, lactoperoxidase, secretory component and lactoferrin will be very useful as pharmaceuticals, cosmetics, foods and drinks, and feeds if they function their biological activities in vivo.

Lactoperoxidase and lactoferrin have been isolated with an alginate gel in a same fraction (Japanese Un-examined Patent Publication No. 246,198 (1986)), with silica particles coated with carboxyl or sulfonyl-type dextran by a salt gradient elution (Japanese Un-examined Patent Publication No. 86,839 (1989)) and with a strong cation exchanger for recovering lactoperoxidase and lactoferrin separately with a step-wise elution by changing salt concentration at pH 6.5 (Republication of International Patent Publication No. 502, 921 (1991)). Furthermore, lactoferrin and lactoperoxidase are isolated separately when milk or whey are mixed with a cation exchange resin, followed by elution of lactoperoxidase with aqueous solutions or buffers having ionic strength of 0.2–0.7 and pH 5 (five) or lower, then elution of lactoferrin with aqueous solutions or buffers with ionic strength of 0.5 or higher and at pH 5 (five) or higher (Japanese Un-examined Patent Publication No. 109,400 (1991)). But no elution of secretory component has been reported.

On the other hand, the present inventors accomplished the isolation of secretory component by contacting milk or whey with a cation exchanger resin, followed by elution with aqueous salt solutions having ionic strength of 0.005–0.25 and pH 6–9 and applied for the patent (Japanese Patent Application No. 49,162 (1991)). This method provides a secretory component rich fraction when milk or whey are adjusted to pH 6–9 and electric conductivity of 6 (six) mS/cm or lower, but the purity was found to be about 70% at maximum. In order to improve the purity of secretory component, residual solution after isolation of lactoferrin and/or lactoperoxidase, are subjected to re-chromatography with an ion exchange resin. Fractionation of secretory component and lactoferrin has been performed with two steps purification procedure; i.e. Firstly using diethylaminoethylcellulose and secondly carboxymethylcellulose (Enomoto fit al., Digestive Organ and Immunology [Shōkaki to Men'eki], 16, 146–150 (1986)). At the industrial scale, the procedure, however, makes the (production) process complicated and the operation efficiency lowers. Furthermore, these processes could not provide simultaneous isolation and purification of biologically active lactoperoxidase, secretory component and lactoferrin in milk and related raw materials.

SUMMARY OF THE INVENTION

This invention has been accomplished on the bases cited above. Milk and related raw materials containing at least one of the lactoperoxidase, secretory component, and lactoferrin are contacted with a cation exchanger to adsorb them, and the adsorbed components are then eluted separately. The process can be efficiently applied to industrial production of lactoperoxidase, secretory component, and lactoferrin.

The inventors had proposed an efficient recovery of lactoperoxidase and lactoferrin in high yields (Japanese Unexamined Patent Publication No. 109,400 (1991)). Because both lactoferrin and secretory component are glycoproteins having molecular weight of about 80 KDa with similar physicochemical properties, it is difficult to distinguish each other by electrophoresis, Therefore, a detailed analysis of the resulted lactoferrin fraction found a co-existing secretory component fraction.

The inventors have investigated to isolate lactoferrin and secretory component from the co-existing fraction, found to selectively and successively elute secretory component and lactoferrin from the fraction by the following process, and accomplished the present invention:

(1) Contact milk and related raw material containing at least one of lactoperoxidase, secretory component, and lactoferrin to a cation exchanger.

(2) Wash the adsorbed cation exchanger with an aqueous solution or a buffer having ionic strength of 0.2 or less and pH 5 (five) or lower.

(3) Selectively elute lactoperoxidase with an aqueous solution or a buffer having ionic strength of 0.2–0.5 and pH 5 (five) or lower.

(4) Selectively elute secretory component with an aqueous solution or a buffer having ionic strength of 0.1–0.5 and pH over 5 (five).

(5) Selectively elute lactoferrin with an aqueous solution or a buffer having ionic strength of over 0.5 and pH over 5 (five).

DETAILED DESCRIPTION OF PREFERRED EMBODIMENT

The milk and related raw materials that can be used for the present invention include milk and whey derived from mammals such as human, cows, water buffaloes, ewes and goats, and mildly heat treated milk is preferably used. Milk powders such as skimmed milk powder, whole milk powder, whey powder, whey protein concentrated powder (WPC) containing whey protein at concentrations of 75% or over, and whey protein isolates powder (WPI) containing whey protein at concentrations of 90% or over may be used after reconstitution. Furthermore, supernatants separated from casein by isoelectric precipitation or casein curds by the addition of a rennet, and a by-produced cheese whey during the production of cheese may also be used. Removal of precipitates from the raw materials by passing through a clarifier, micro-filtration or conventional filtration is preferable for the process of the present invention to improve the adsorption efficiency to the ion exchanger and the purity of the products.

The milk and related raw materials used for the present invention shall contain at least one of lactoperoxidase, secretory component and lactoferrin.

Milk and related raw materials having pH 4–9 are preferred to contact with a cation exchanger for successful isolation of lactoperoxidase, secretory component, and lactoferrin in high yield. Milk containing casein causes unfavorable precipitation of casein at pH less than 5 (five), and whey having pH less than 4 (four) causes adsorption of contaminants such as β-lactoglobulin, α-lactalbumin, serum albumin, immunoglobulin in the cation exchanger together with lactoperoxidase, secretory component, and/or lactoferrin and decline of the amounts and purity of lactoperoxidase, secretory component, and/or lactoferrin. Additionally, the activity of lactoperoxidase reduces significantly at pH less than 4 (four). Milk or whey having pH over 9 (nine) reduces the amounts of adsorbed lactoperoxidase, secretory component, and lactoferrin in the cation exchanger.

Milk and related raw materials containing at least one of lactoperoxidase, secretory component, and lactoferrin may be adsorbed without desalting or adjustment of the ionic strength, but extensive desalting down to 5 (five) mS/cm or lower of electric conductance improves the adsorption of secretory component to the cation exchanger.

Cation exchangers for the adsorption of lactoperoxidase, secretory component, and/or lactoferrin include cross linked polysaccharides and cellulose, and acrylamide resins directly or indirectly introduced, via proper spacer with carboxyl, sulfonic or phosphoric acid residues optionally interrupted with a spacer. Practically, CM-cellulofine C-500 (Seikagaku Corp.) introduced with carboxymethyl group, sulfonated Chitopearl (Chitopearl-SU) (Fuji Spinning Co., Ltd.) introduced with sulfonic group, SP-Toyopearl 550C (TOSOH Corp.) and S-Sepharose FF (Pharmacia Biosystems Corp.) introduced with sulfopropyl group, and phosphocellulose introduced with phosphoric acid group can be illustrated.

Contact of milk and related raw materials containing at least one of lactoperoxidase, secretory component, and lactoferrin with a cation exchanger is performed by various methods, such as mixing both materials in a tank, passing the raw material through a column packed with the cation exchanger, or an application of a rotary column reactor (Japanese Un-examined Patent Publication No. 138,295 (1990)). The rotary column reactor is preferable for the efficient mass production.

The temperature for the contact of the milk and related raw materials containing at least one of lactoperoxidase, secretory component, and lactoferrin with the cation exchanger has no particular limit, but generally temperatures between 4° C. and lower than 60° C. are used. Temperatures lower than 4° C. risk the raw materials to freeze, and increase in viscosity, or in some cases result in separation of fat, and temperatures 60° C. or over may denature lactoperoxidase, secretory component, and lactoferrin. Temperatures of 15° C. or over stimulate the proliferation of microorganisms, thus temperatures of less than 15° C. are preferable for the treatment of large amount of milk and related raw materials.

One kg of a milk and related raw material and 0.2–100 g of a cation exchanger may generally be mixed and the resultant mixture is stirred for 15 minutes to 15 hrs.

The elution of adsorbed lactoperoxidase, secretory component, and lactoferrin is carried out as follows.

The cation exchanger is washed with an aqueous solution and a buffer having ionic strength of 0.2 or less and pH 5 (five) or lower to remove impurities that are clogged between the particles of the exchanger. Solutions or buffers having ionic strength over 0.2 or pH over 5 (five) may cause the elution of lactoperoxidase adsorbed in the cation exchanger, therefore, ionic strength of 0.05–0.15 and pH 4–5 are preferable for the washing. Prior to the washing, pretreatment of the cation exchanger adsorbing lactoperoxidase, secretory component, and/or lactoferrin with an aqueous solution or a buffer having ionic strength of 0.1 or less and pH over 5 (five) may be performed. Both cold and warm water can be used for the washing. Thorough pre-washing may save the volume of aqueous solution or buffer having ionic strength of 0.2 or less and pH 5 (five) or lower which will be used in the following washing and is economical. There is no particular limit in an aqueous solution or a buffer used for washing except for ionic strength of 0.2 or less and pH 5 (five) or lower. Practically, organic acid buffers such as acetate, citrate and dimethylglutarate, and glycine buffer can be used. A phosphate buffer may be used also, but it shows insufficient buffer action at pH 5 (five) or lower.

Then, lactoperoxidase, secretory component, and/or lactoferrin adsorbed in the cation exchanger are selectively separated and eluted. In the present invention, lactoperoxidase, secretory component, and lactoferrin can be effectively separated and eluted with only one chromatographic procedure by a combination of washing with a particular ionic strength and pH and elution with an eluting solution having different particular ionic strength and pH.

A fraction containing lactoperoxidase, secretory component, and lactoferrin can also be obtained by elution with an aqueous solution or a buffer having pH over 5 (five) and ionic strength over 0.5.

Lactoperoxidase adsorbed in the cation exchanger is eluted with an aqueous solution or a buffer having ionic strength of 0.2–0.5 and pH 5 (five) or less, preferably ionic strength of 0.2–0.4 and pH 3–5. Lactoperoxidase is not or hardly be eluted at an ionic strength of 0.2 or less. Secretory component and lactoferrin are simultaneously eluted at ionic strength of 0.5 or over regardless of pH 5 (five) or less and affect the purity of lactoperoxidase and recovery of secretory component and lactoferrin. On the contrary, a small amount of secretory component and lactoferrin are eluted in a same fraction at pH 5 (five) or over regardless of ionic strength of 0.2 or less and the purity of lactoperoxidase declines. The aqueous solution and buffer used for the elution have no particular limit and include buffers of organic acids such as acetate, citrate and dimethylglutarate, and glycine buffer can be used. Sodium chloride may be added to increase the ionic strength. The resultant lactoperoxidase solution has purity of at least 50% or over and lactoperoxidase with purity of 80% or over can be normally obtained.

Elution with an aqueous solution or a buffer having pH over 5 (five) and ionic strength of 0.1–0.5 provides a fraction containing both lactoperoxidase and secretory component.

Following the elution of lactoperoxidase, elution of secretory component adsorbed in the cation exchanger is performed with an aqueous solution or a buffer having ionic strength 0.1–0.5, preferably 0.3–0.5 and pH over 5 (five), preferably pH 6–8. Elution at pH 5 (five) or lower makes the separation of secretory component and lactoferrin difficult and declines the purity of secretory component. Elution at ionic strength over 0.5 increases contamination with lactoferrin and affects the purity of secretory component. There is no particular definition for the aqueous solution or buffer for the elution and phosphate, imidazole, Tris and acetate buffers can be enumerated. Thus, secretory component having purity of 80% or over can be easily obtained.

Elution with an aqueous solution or a buffer over pH 5 (five) and ionic strength over 0.5 provides a fraction containing both secretory component and lactoferrin.

Elution of lactoferrin from the adsorbed cation exchanger following the elution of lactoperoxidase and secretory component is performed with an aqueous solution or a buffer having ionic strength over 0.5, preferably 0.7–2.0 and pH over 5 (five), preferably 6–8. Ionic strength of 0.5 or less, or pH 5 (five) or less decrease the amount of lactoferrin in the eluate. The aqueous solution and buffer used for the elution have no particular qualification and an aqueous solution or a buffer of organic acid such as citrate, acetate and maleate, and phosphate, imidazole, sodium bicarbonate, borate and Tris buffers added with sodium chloride to make ionic strength over 0.5 can be illustrated. The resultant lactoferrin solution has purity of at least 70% or over and lactoferrin having purity of 80% or over can be normally obtained.

Prior to the elution of lactoperoxidase, secretory component, and lactoferrin with an aqueous solution or a buffer, washing with an aqueous solution or buffer having ionic strength of less than 0.1 and a pH same as those of eluting solution can be employed. Although this washing process is time-consuming it is effective to wash-out salts remaining in the cation exchanger and to equilibrate the pH of the cation exchanger to the aimed condition. This procedure is, thus, effective for the satisfactory selective elution.

cation exchanger used for adsorption and elution of lactoperoxidase, secretory component, and/or lactoferrin can be recycled by washing with an aqueous solution and a buffer having ionic strength of over 0.25 followed by thorough washing with water.

The outline of the process of the present invention is shown in Table 1.

TABLE 1

Milk and related raw material

Eluting solution (1)
(b)
Eluting solution (2)
Eluting solution (3)
Eluting solution (4)
Eluting solution (5)
Eluting solution (b)

(e) (d) (c) (a)

| Eluting solution | Ionic strength | pH |
| --- | --- | --- |
| (1) | <0.2 | ≦5 |
| (2) | 0.2–0.5 | ≦5 |
| (3) | 0.1–0.5 | >5 |
| (4) | >0.5 | >5 |

TABLE 1-continued

| (5) | ≧0.25 | |
| --- | --- | --- |
| (a) | Lactoperoxidase, secretory component, and lactoferrin free milk or whey | |
| (b) | Waste solution | |
| (c) | Lactoperoxidase eluate fraction | |
| (d) | Secretory component eluate fraction | |
| (e) | Lactoferrin eluate fraction | |

The resultant lactoperoxidase, secretory component, and/or lactoferrin solutions are concentrated, desalted or dried, if necessary. The concentration is carried out by various methods such as evaporation under vacuum, ultra-filtration and reverse osmotic pressure filtration. The desalination is performed by conventional methods and techniques such as ultrafiltration, dialysis tube, electrodialysis, ion-exchanger resin and gel filtration. The drying i s done by lyophilization, spray drying and so forth.

Immunoglobulin may present in the solution or dried lactoperoxidase and secretory component as an impurity. Further purification of these proteins can be accomplished by a chromatography using a carrier matrix immobilized with protein G or A to remove immunoglobulin G from the recovered lactoperoxidase or secretory component. These purification procedures yield lactoperoxidase and secretory component at purity of 90% or over.

The present invention will be explained more in detail by the following examples.

[EXAMPLE 1]

Six hundred g of cheese whey was desalted with an ultrafiltration membrane having molecular weight cut-off of 20,000 down to two mS/cm. The desalted cheese whey (pH 6.4) contained 22, 17, and 48 g of lactoperoxidase, secretory component, and lactoferrin, respectively. The desalted whey was mixed with six kg of SP-Toyopearl 550° C. (TOSOH Corp.) and contacted with stirring for six hrs. in a tank to adsorb lactoperoxidase, secretory component, and lactoferrin in the cation exchanger. The mixture was allowed to stand to precipitate the adsorbed exchanger and the supernatant was removed by decantation and the remaining cation exchanger was packed in a column (diameter 20 cm×height 29 cm).

The packed column was thoroughly washed with water, equilibrated with five mM citrate buffer (pH 5.0), and washed with five mM citrate buffer containing 0.08M of NaCl (pH 5.0). The elution of lactoperoxidase was performed with five mM of citrate buffer containing 0.3M of NaCl (pH 5.0). Following the elution of lactoperoxidase, the column was equilibrated with 10 mM citrate buffer containing 0.01M NaCl (pH 6.5), and secretory component was eluted with 0.4M aqueous NaCl solution, then lactoferrin was eluted with one M of NaCl aqueous solution.

The eluted lactoperoxidase, secretory component, and lactoferrin solutions were concentrated and desalted with an ultrafiltration membrane having molecular weight cut-off of 10,000, respectively, and lyophilized to give 18 g of lactoperoxidase at purity of 87%, 15.3 g of secretory component at purity of 90%, and 35 g of lactoferrin at purity of 92%. The determination of purity was performed with sodium dodecyl sulfate-polyacrylamide gel electrophoresis (SDS-PAGE).

[EXAMPLE 2]

In a tank. 200 kg of cheese whey and two kg of S-Sepharose FF (Pharmacia Biosystems Corp.) were placed and the resultant mixture was stirred to contact them for 15 hrs., and lactoperoxidase, secretory component, and lactoferrin were adsorbed to the cation exchanger. The mixture was allowed to stand to precipitate the absorbed exchanger and the supernatant was removed by decantation. The resultant exchanger was packed in a column (diameter 20 cm×height 29 cm).

The packed column was washed thoroughly with water, equilibrated with 10 mM citrate buffer (pH 4.0), and washed with 10 mM citrate buffer containing 0.15M NaCl (pH 4.0). Lactoperoxidase was eluted with 10 mM citrate buffer containing 0.4M NaCl (pH 4.0). After the elution of lactoperoxidase, the column was equilibrated with 10 mM citrate buffer (pH 6.5) and secretory component was eluted with 0.4M NaCl aqueous solution. Then, lactoferrin was eluted with one M NaCl aqueous solution.

The eluted lactoperoxidase, secretory component, and lactoferrin solutions were concentrated and desalted with an ultrafiltration membrane having molecular weight cut-off of 10,000, respectively, and lyophilized to give 12 g of lactoperoxidase at purity of 90%, eight g of secretory component at purity of 85%, and 17 g of lactoferrin at purity of 95%.

[EXAMPLE 3]

In a rotary column reactor (Tokyo Rika Kikai Co., Ltd.) packed with 1.5 L of sulfonated Chitopearl (Chitopearl-SU) (Fuji Spinning Co., Ltd.), 400 kg of fresh skimmed milk (pH 6.8) was cycled for three hrs. at a flow rate of 200 L/hr. The treated rotary column reactor together with the resin was thoroughly washed with warm water at a temperature of 40° C. and five mM acetate buffer containing 0.07M of KCl (pH 4.0), successively. Lactoperoxidase was eluted from the column with 0.2M KCl aqueous solution adjusted to pH 4.0 with HCl Then the column together with the resin was thoroughly washed with water, 0.01M Tris-HCl buffer (pH 7.5) and 0.3M KCl aqueous solution, successively. Lactoferrin was eluted with sodium bicarbonate buffer containing 0.75M KCl (pH 7.5).

The eluted lactoperoxidase, secretory component, and lactoferrin solutions were concentrated separately using an ultrafiltration membrane having molecular weight cut-off of 50,000 down to 1.5 L volume, desalted to give electroconductivity of 0.2 mS/cm with an electrodialysis membrane and lyophilized to give 19.7 g of lactoperoxidase at purity of 85%, 13.8 g of secretory component at purity of 88%, and 39 g of lactoferrin at purity of 94%. The purity was determined with SDS-PAGE method.

[EXAMPLE 4]

In 250 ml of water, 15 g of whey protein concentrate (WPC) was dissolved, adjusted to pH 7.5, then passed through a column (diameter 1.5 cm×height 12 cm) packed with 10 g of CM-Cellulofine (Seikagaku Corp.).

The packed column was thoroughly washed with 0.005M phosphate buffer (pH 7.5) and 0.005M citrate buffer containing 0.05M NaCl (pH 4.5), successively. Lactoperoxidase was eluted with 0.005M citrate buffer containing 0.25M NaCl (pH 4.5). Secretory component was eluted with a 0.01M phosphate buffer containing 0.15M NaCl (pH 7.0). Lactoferrin was eluted with 0.01M phosphate buffer containing 0.7M NaCl (pH 7.0).

The eluted lactoperoxidase, secretory component, and lactoferrin fractions were desalted with a desalting ion exchanger resin Amberlite MB-3 (Rohm & Haas Japan) down to the electroconductivity of 0.5 mS/cm, concentrated and lyophilized to give five mg of lactoperoxidase at of purity 91%, two mg of secretory component at purity of 96%, and eight mg of lactoferrin at purity of 96%. The purity was determined with SDS-PAGE.

The isolation and purification of lactoperoxidase, secretory component, and lactoferrin by the present invention, requires no repeated chromatographic isolation and purification procedures and can be performed by simple methods. That is, the present invention gave lactoperoxidase, secretory component, and lactoferrin at purity of 80% or over in a single chromatographic treatment. Additional treatment with an ultrafiltration eliminates a small amount of low molecular weight fraction and provides lactoperoxidase, secretory component, and lactoferrin at purity of 85% or over. The simplified process provides not only highly pure lactoperoxidase, secretory component, and lactoferrin at high yield but also reduces production cost. The products can be used for foods and pharmaceuticals for the treatment and prevention of infectious diseases and anemia.

We claim:

1. A process for separating lactoperoxidase, secretory component and lactoferrin from milk or whey using a single cation exchange resin which binds lactoperoxidase, secretory component and lactoferrin, said process comprising:

a. contacting the milk or whey with said cation exchange resin for about 15 minutes to about 15 hours thereby causing any lactoperoxidase, secretory component or lactoferrin contained therein to become adsorbed to said cation exchange resin;

b. washing said cation exchange resin with an aqueous solution having an ionic strength of less than about 0.2 and a pH of about 5 or lower, then sequentially;

c. first eluting said lactoperoxidase by contacting the cation exchange resin with an aqueous solution having an ionic strength of from about 0.2 to about 0.5 and a pH of 5 or lower thereby forming an eluate containing lactoperoxidase;

d. second eluting said secretory component by contacting the cation exchange resin with an aqueous solution having an ionic strength of from about 0.1 to about 0.5 and a pH higher than 5 thereby forming an eluate containing secretory component; and e. third eluting said lactoferrin by contacting the cation exchange resin with an aqueous solution having an ionic strength higher than about 0.5 and a pH higher than 5 thereby forming an eluate containing lactoferrin;

wherein the lactoperoxidase, secretory component and lactoferrin obtained in steps (c), (d) and (e) each have a purity of about 80% or greater.

2. The process according to claim 1, wherein said milk or whey is derived from mammals.

3. The process according to claim 1, wherein said milk or whey has a pH of from about 4 to about 9.

4. The process according to claim 1, wherein said milk or whey has an electroconductivity of about 5 mS/cm or less.

5. The process according to claim 1, wherein said cation exchange resin is selected from the group consisting of cellulose, and acrylamide resin having carboxyl, sulfonic acid or phosphoric acid functional groups.

6. The process according to claim 1, wherein step (a) is performed at a temperature of from about 4° C. to about 60° C.

7. The process according to claim 1, wherein in step (a) the ratio of said milk or whey to the cation exchange resin is approximately 1 kg to 0.2–100 g, respectively.

8. The process according to claim 1 wherein said cation exchange resin is washed with an aqueous solution having an ionic strength of about 0.1 or less and a pH over 5 prior to step (b).

9. The process according to claim 1, wherein said eluate containing lactoperoxidase, secretory component or lactoferrin is concentrated, desalted, and dried to powder.

10. The process according to claim 1 wherein said cation exchange resin is a cross-linked polysaccharide having carboxyl, sulfonic acid or phosphoric acid functional groups.

11. The process according to claim 5 wherein a spacer is between the cellulose or acrylamide resin and the functional groups.

12. The process according to claim 10 wherein a spacer is between the cross-linked polysaccharide and the functional groups.

* * * * *